United States Patent
Brandt et al.

(10) Patent No.: US 8,414,532 B2
(45) Date of Patent: Apr. 9, 2013

(54) MODULAR DRUG DELIVERY DEVICE FOR ADMINISTERING DISCRETE DOSES OF A MEDICAMENT

(75) Inventors: Derek Brandt, Oberdorf (CH); Irio Calasso, Arth (CH)

(73) Assignee: Sensile Pat AG, Haegendorf (CH)

( * ) Notice: Subject to any disclaimer, the term of this patent is extended or adjusted under 35 U.S.C. 154(b) by 0 days.

(21) Appl. No.: 12/672,003

(22) PCT Filed: Aug. 4, 2008

(86) PCT No.: PCT/IB2008/053113
§ 371 (c)(1),
(2), (4) Date: Feb. 3, 2010

(87) PCT Pub. No.: WO2009/019648
PCT Pub. Date: Feb. 12, 2009

(65) Prior Publication Data
US 2011/0196337 A1    Aug. 11, 2011

(30) Foreign Application Priority Data
Aug. 7, 2007  (EP) .................................. 07405230

(51) Int. Cl.
*A61M 5/14*    (2006.01)

(52) U.S. Cl.
USPC ...... 604/131; 604/890.1; 604/151; 604/93.01

(58) Field of Classification Search .............. 604/890.1, 604/131, 140–143, 151, 21, 65, 93.01, 891.1
See application file for complete search history.

(56) References Cited

U.S. PATENT DOCUMENTS

| | | | |
|---|---|---|---|
| 4,277,226 A * | 7/1981 | Archibald | ........................ 417/38 |
| 4,734,092 A | 3/1988 | Millerd | |
| 4,886,499 A * | 12/1989 | Cirelli et al. | ................... 604/131 |
| 2002/0169439 A1 | 11/2002 | Flaherty | |
| 2004/0204673 A1* | 10/2004 | Flaherty | ........................... 604/65 |
| 2006/0184119 A1 | 8/2006 | Remde et al. | |
| 2008/0129486 A1 | 6/2008 | Jeckelmann et al. | |

FOREIGN PATENT DOCUMENTS

| | | |
|---|---|---|
| EP | 1 527 793 | 5/2005 |
| WO | WO 2004/110526 | 12/2004 |
| WO | WO 2006/114297 | 11/2006 |
| WO | WO 2007/000427 | 1/2007 |

OTHER PUBLICATIONS

Written Opinion in International Application No. PCT/IB2008/053113, Nov. 18, 2008, pp. 1-9.

* cited by examiner

*Primary Examiner* — Laura Bouchelle
(74) *Attorney, Agent, or Firm* — Saliwanchik, Lloyd & Eisenschenk

(57) ABSTRACT

There provided a drug delivery device adapted for providing a plurality of discrete doses of a medicament including a disposable delivery unit (2) adapted to be worn by a user, comprising a reservoir (10b) for holding a medicament to be delivered, an injection member (22) adapted for trans-dermal drug delivery, and a pump (12) adapted for pumping the medicament to be delivered from the reservoir (10b) to the injection member (22); and a separate reusable base unit (4) comprising a drive module for driving the pump (12). The pump in the disposable delivery unit is activated to deliver a dose of the medicament by bringing the base unit temporarily into communication with the delivery unit.

23 Claims, 4 Drawing Sheets

MODULAR DRUG DELIVERY DEVICE FOR ADMINISTERING DISCRETE DOSES OF A MEDICAMENT

CROSS-REFERENCE TO RELATED APPLICATION

This application is the U.S. national stage application of International Patent Application No. PCT/IB2008/053113, filed Aug. 4, 2008, the disclosure of which is hereby incorporated by reference in its entirety, including all figures, tables and amino acid or nucleic acid sequences.

The present invention relates to a drug delivery device, particularly to a drug delivery device suitable for delivering discrete doses of a medicament. The medicament may in particular be insulin for diabetic patients.

Regular trans-dermal administration of doses of a medicament is necessary in the control or therapy of many conditions, such as diabetes, growth hormone deficiency, pain therapy, and chemotherapy. For instance diabetic patients may require injections of insulin several times a-day. The insulin dosage regime required for a diabetic patient varies dependent on a number of factors including for instance the type of diabetes, the type of insulin administered, the actual severity of the condition, the lifestyle of the patient, the routine and diet of the patient. Accordingly diabetic patients often need to administer doses of insulin themselves, several times a day, and in places other than hospitals or medical centres.

A number of devices have been proposed to facilitate self-administration of doses of a medicament. One type of such devices is often referred to as patch devices. Patch devices are directly attached to the skin of the patient.

WO 2004/110526 A1 discloses a modular infusion pump for administration of a product. The infusion pump contains an injection module and a pump module, which are both located close to the injection site. The pump module contains a reservoir, a motor, and a pump unit. The pump unit is configured for delivering the product from the reservoir to the injection module, which is connected to the pump module. A third module contains an energy source, which is connected to the pump module in order to supply the pump module with energy.

EP 1527793 A1 discloses a pump system for the subcutaneous delivery of liquid medicament, with a pump module and a motor section. This pump system, comprising a pump module and a motor section, is compact and may therefore be fixed directly to the site of injection, e.g. in the form of a patch.

WO 2007/000427 A1 discloses a user input device for operating a drug delivery system. The user input device communicates with a patch device. The patch device contains a reservoir and an expelling assembly to expel the drug out of the reservoir.

WO 2006/114297 A1 discloses a system for energy-optimized data transmission for a medical appliance. One unit positioned in or on the body contains an activation switch which is switched on when an activation signal is received from the second external unit. The first unit may remain in a non-operative condition until an activation signal is received, such that energy consumption is optimized.

U.S. Pat. No. 4,734,092 discloses an ambulatory drug delivery device in the form of a patch, comprising a two-part housing. The first part containing the pump module is a reusable unit, and the second part containing a spiral fluid reservoir, a filter, and a semi-pivoting cannula is a disposable unit.

Beside patch devices, a number of pen-type injection devices have been developed to facilitate the self-administration of medicaments such as insulin. Typically such injection pen devices include a vial holder in the form of an elongate tube into which a vial containing a medication, such as insulin, may be loaded. At one end of the vial holder is mounted a double-ended needle assembly, and at the opposed end of the vial holder is mounted a plunger connected to a piston rod for driving the plunger. The vial holder is mounted in a pen body which includes a dose setting means for setting the dose to be delivered, and a drive means for pushing the plunger through a distance corresponding to the dose setting. On use a vial containing the medication is inserted into the vial holder such that a septum in the form of an elastic sealing membrane on the medicament vial is pierced by the needle assembly. The pen body is then connected to the vial holder and the patient operates the drive means to push the plunger forwards to deliver the pre-set dose of medicament. After each use the patient discards the double-ended needle assembly, and retains the pen for the next dose administration. On each use a new double-ended needle assembly is mounted on the pen and the patient makes a new injection. After a number of dose administrations the vial is emptied and must be discarded. The patient removes the vial from the vial holder, inserts a new vial and reassembles the pen for further use.

Such injection pen devices allow a patient to self-administer doses of a medicament, such as insulin, more easily and more conveniently than with a standard hypodermic syringe and vial. The pen-type injection devices however have a number of drawbacks.

A patient using such an injection pen device is obliged to re-assemble the pen device at each use, mounting a new needle assembly into the pen for each use. The medicament vial must also be removed and replaced each time a vial is exhausted. Such manipulations are inconvenient and introduce a source of risk of contamination.

Further, for each dose of medicament required by the patient, the patient is obliged to make a new injection. Thus a patient may be obliged to make several injections over the course of a day. The requirement to make repeated injections is inconvenient for the patient, particularly where they need to administer their medication in a public place, and can introduce in a patient a fear of administration of their medication. It is also a problem to accumulate multiple injection points on the patient's body, making it more difficult to carry out further injections.

The known injection pen devices generally have a very basic mechanical dosage measuring facility, and lack effective means for accurately measuring and regulating dose amounts, or for monitoring the time between doses and/or the number or amount of doses over period of time.

There is accordingly an ongoing need to provide alternative drug delivery devices that are convenient for use by a patient and enable safe, efficient and discrete administration of required doses of a medicament such as insulin.

In view of the above, an object of the invention is to provide a drug delivery device for providing discrete doses of a medicament that overcomes the above-mentioned drawbacks of the present pen-type injectors.

It is an object of the invention to provide a drug delivery device that is portable, easy to use, and does not require complex manipulations by the user.

It would be advantageous to provide a drug delivery device that is accurate, reliable, compact and very safe to use.

It would be advantageous to provide a drug delivery device that is cost effective to manufacture, such that it may be manufactured, at least in part, as a disposable device.

Objects of the invention are achieved by a drug delivery device according to claim 1.

Disclosed herein is a drug delivery device, in particular adapted for providing a plurality of discrete doses of a medicament, including a disposable delivery unit adapted to be worn by a user, and a separate reusable base unit. The disposable delivery unit comprises a reservoir for holding a medicament to be delivered, an injection member adapted for trans-dermal drug delivery, and a pump adapted for pumping the medicament to be delivered from the reservoir to the injection member. The separate reusable base unit comprises a drive module for driving the pump. The pump in the disposable delivery unit is activated to deliver a dose of the medicament by docking the base unit temporarily on the delivery unit such that the base unit is in power communication with the delivery unit to drive the pump. In the present, the term "trans-dermal" is to be understood in its broadest sense and intended to include any type of drug delivery into or traversing the skin, including subcutaneous, intramuscular, intra-peritoneal, intravenous, spinal, intra-articular, and intra-dermal.

The delivery unit is compact and conveniently worn by a user. Advantageously the disposable delivery unit comprises an adhesive base adapted for removable adhesive mounting of the delivery unit on a user's skin. The injection member may be in the form of a needle, a canula inserted with a removable needle, or a catheter suitable for trans-dermal drug delivery. The delivery unit may be provided without a battery, such that the delivery unit may be disposed of conveniently and environmentally friendly.

The delivery unit of the present invention may be worn by a user for a period of time, for example a few days, e.g. 1 to 7 days, suitably 2 to 3 days. Advantageously the drug delivery device of the present invention allows the user to self-administer multiple discrete doses of a medicament, for example bolus insulin doses, without having to make a new injection each time a dose of medicament is required. The drug delivery device is accordingly discrete and convenient to use.

The pump, medicament reservoir and injection member parts are all contained in the delivery device. The delivery unit is of simple construction, does not contain any power supply for the pump, and may be manufactured using readily available, inexpensive materials and methods, allowing it to be manufactured as a disposable unit. Advantageously this disposable delivery unit is provided as a closed unit which is discarded after use, avoiding the need for complex manipulations by the user, and the associated risks of contamination, in carrying out replacement of a needle unit and/or medicament vial. Alternatively, the disposable delivery unit could also be filled with medicament or an excipient just before use with a needle through a septum. The latter embodiment may be employed for medications, such as growth hormone, that are stored in powder form in the delivery unit to increase shelf life, and to which an excipient is added by the patient before use.

In a preferred embodiment the pump is activated by bringing the base unit over and pressing against the drive module of the delivery unit, either directly or through a layer of clothing. According to the drug delivery device of the present invention, no mechanical connection or mounting is required between the base unit and the delivery unit for activating the pump. Accordingly the delivery device is very convenient, easy and safe to use. The base unit is advantageously of dimensions suitable for easy transport by a patient, and may conveniently be carried e.g. in a pocket or handbag. The base unit may in addition also communicate information with the delivery unit for monitoring and control purposes.

According to a preferred embodiment the driving force for driving the pump may be provided by electromagnetic power communication between a rotor on the pump and a stator in the drive module. Advantageously the drive force may be provided by electromagnets on the stator in the drive module, driving permanent magnets located on the pump rotor. A suitable pump system is provided by the micropump described in international patent application WO 2005 039674, the contents of which are incorporated herein by reference. The micropump described in WO 2005 039674 is well adapted for the subcutaneous delivery of liquid medicaments such as insulin. It is precise, compact, portable and reliable because of the simplicity of its construction and its particular functioning principle. Alternatively, the drive force may be provided by rotating permanent magnets or a rotating magnetic field produced by coils in the base unit that drive permanent magnets in the pump rotor. An alternating magnetic field generated in the base unit by moving magnets or by coils may alternatively also drive the pump by inducing electrical power in coils in the delivery unit that supplies the pump with drive power and supply power to electronic components in the delivery unit.

Preferably the base unit contains a power supply and electronics for controlling and monitoring the operation of the pump. Advantageously the base unit comprises a user interface, suitably in the form of one or more buttons and a display, to allow the user to set the required dose of medicament and/or to obtain information on blood sugar levels and/or to set alarm levels or to time reminders.

In a preferred embodiment the base unit contains a memory device, suitably comprising an electronic memory chip, adapted to monitor one or more of the time elapsed since at least a last delivered dose, the amounts of at least a last delivered dose, and/or the number and/or amount of doses administered over a certain time period, e.g. a day. In this way a user can easily and conveniently monitor the administration of their medicament, e.g. of bolus insulin doses.

The memory device may optionally provide an alarm function by which a user may be notified, e.g. by a visual, a vibrating, or audible alarm contained in the base unit, if the delivery unit has been activated to deliver doses of mendicant too frequently or too infrequently. The user interface may advantageously provide a function for setting and regulating the alarm function by the user.

There is also provided a method for the treatment of a condition or disease requiring the administration of discrete doses of a medicament, comprising removably fixing to the skin of a patient in need thereof a disposable delivery unit comprising a reservoir for holding a medicament to be delivered, an injection member adapted for trans-dermal drug delivery, and a pump adapted for pumping the medicament to be delivered from the reservoir to the injection member; and bringing a separate reusable base unit which comprises a drive module for driving the pump temporarily into power communication with the delivery unit, such that the pump is activated to deliver a dose of the medicament to the patient.

Further disclosed herein is a method of bolus administration of a medicament to a patient in need thereof comprising providing a disposable delivery unit adapted to be worn by a patient and comprising a reservoir for holding a medicament to be delivered, an injection member adapted for trans-dermal drug delivery, and a pump adapted for pumping the medicament to be delivered from the reservoir to the injection member, providing a separate reusable base unit comprising a drive module for driving the pump, removably fixing said delivery unit to a patient's skin, and bringing the base unit temporarily into close proximity with the delivery unit such that the pump is activated to deliver a dose of the medicament to the patient.

The method of the present invention allows for the convenient, safe and discrete self-administration to a patient of multiple discrete doses of a medicament requiring trans-dermal administration, such as bolus insulin injection.

There is also provided a method for operating a drug delivery device adapted for providing a plurality of discrete doses of a medicament, comprising removably fixing to a user's skin a disposable delivery unit comprising a reservoir for holding a medicament to be delivered, an injection member adapted for trans-dermal drug delivery, and a pump adapted for pumping the medicament to be delivered from the reservoir to the injection member; and bringing a separate reusable base unit, comprising a drive module for driving the pump, temporarily into communication with the delivery unit such that the pump is activated to pump a dose of medicament from the reservoir to the injection member.

Further objects and advantageous aspects of the invention will be apparent from the claims and the following detailed description of an embodiment of the invention in conjunction with the drawings in which:

Figure 1:
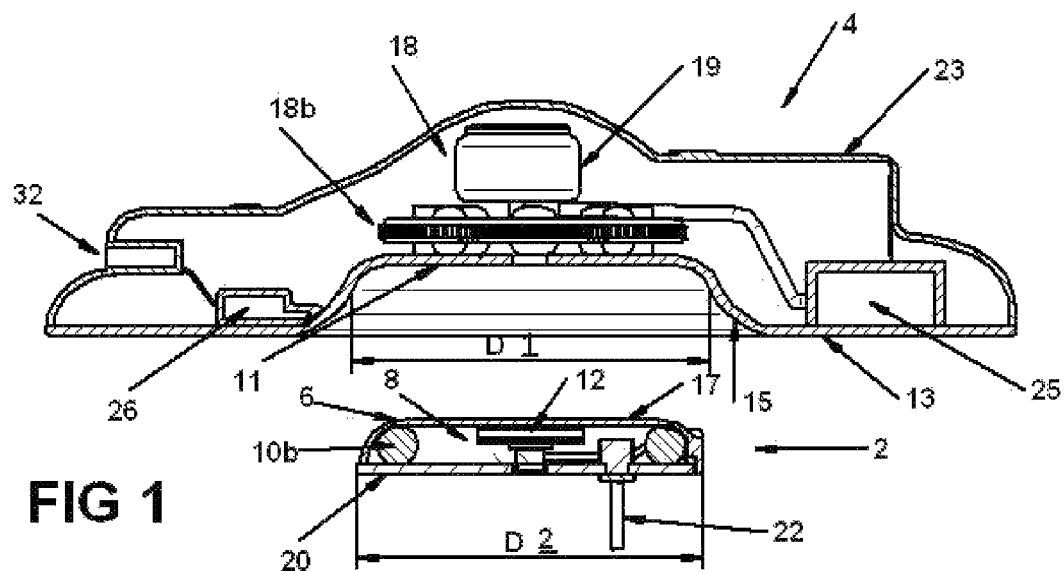
FIG. 1 shows a cross-sectional view of drug delivery device with a reusable base unit and a disposable delivery unit according to an embodiment of the invention.
Figure 2:
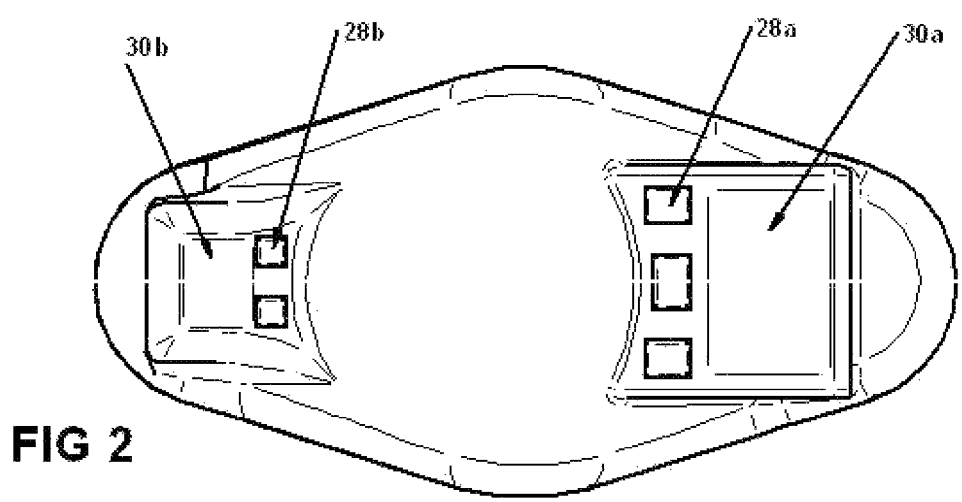
FIG. 2 shows a top view of a base unit of the delivery device according to an embodiment of the invention.

Referring to FIG. 1, an embodiment of a drug delivery device according to the present invention comprises a disposable delivery unit 2 and a reusable base unit 4.

The delivery unit 2 comprises a housing 6, defining a chamber 8, in which is contained a reservoir 10a, 10b for holding the liquid medicament and a pump 12. The reservoir is advantageously mounted to a pump module 12 as a single unit. Any suitable type of reservoir may be envisaged.

Figure 5:
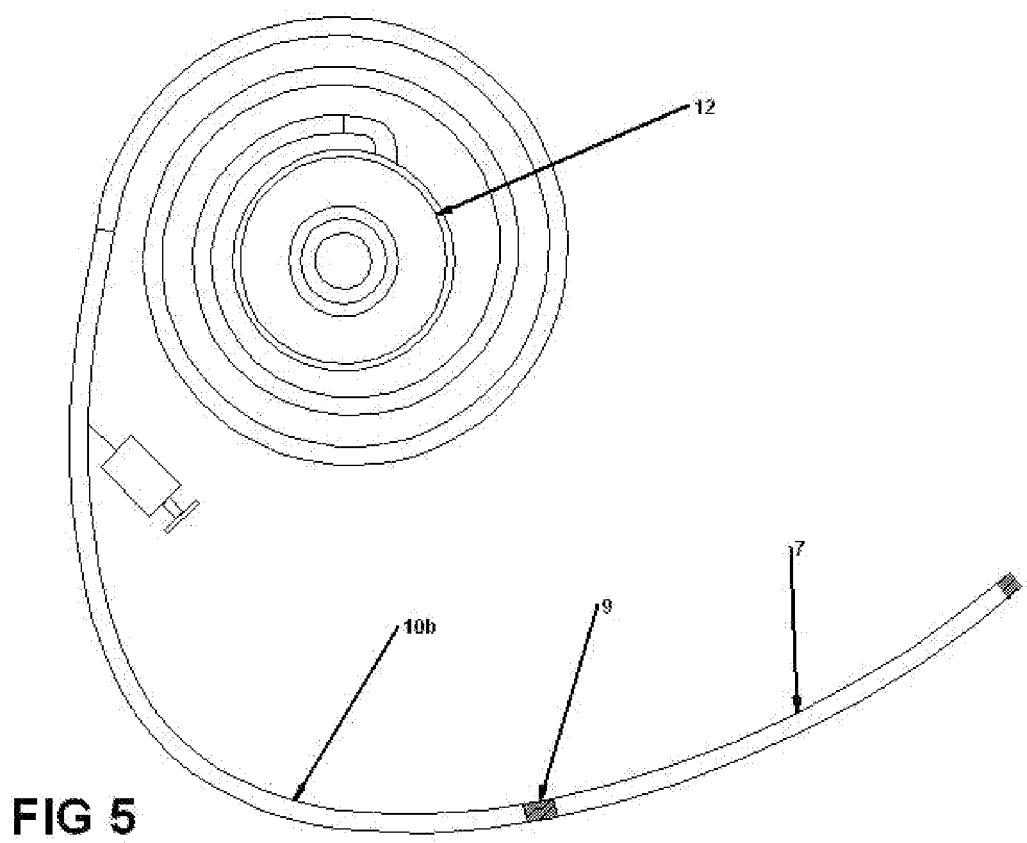
FIG. 5 shows a view of a pump and coil reservoir (shown unwound) of an embodiment of the delivery unit.

Advantageously the reservoir may be a collapsible reservoir 10a or a coil-type reservoir 10b. According to an embodiment of the invention, as shown in FIG. 5, the coil-type reservoir 10b is attached to the pump 12 which may be filled with a syringe. In order to allow air present in the reservoir to escape, a hydrophobic membrane 9 is provided in the end of the reservoir section, which allows air to pass but not the liquid medicament. In addition, it is possible to provide a closed chamber 7 in which gas is compressed when the reservoir 10b is filled. The compressed gas then will convey the liquid drug towards the pump 12. The walls of the chamber 7 may be provided in flexible material, so that the chamber expands upon filling of the reservoir 10b. If the walls of the chamber 7 are provided in inflexible material, the volume of the chamber 7 should be at least as large as the volume of the reservoir 10b, in order to keep the fluid pressure on the pump 12 in a range that does not cause leakage in the pump valves.

Alternatively, a coil-type reservoir 10b may be provided without a hydrophobic membrane. In this embodiment, the reservoir is closed and has a diameter that does not allow air bubbles to move freely due to capillary effects, the diameter may typically measure between 1 and 5 mm.

The pump may be any suitable type of pump adapted for the delivery of accurate amounts of a medicament for trans-dermal delivery. Advantageously the pump may be a micro-pump as described in the earlier international patent application WO 2005 039674, which is incorporated herein by reference.

The delivery unit 2 may contain a capacitor (not shown) adapted to trigger an alarm if a parameter of the delivery unit 2 is outside a predefined range. The capacitor may be provided with electrical energy from the reusable base unit 4, such that the delivery unit 2 may not contain a battery. Typical parameters of the delivery unit may be the filling level of the reservoir 10a, 10b, leakage or occlusion of the pump 12, or air bubbles in the reservoir.

The re-usable base unit 4 comprises a housing 23, a power supply 24, a drive module 18 and electronics 26 for controlling and operating the drive module for operation of the pump. The drive module comprises a varying magnetic field generation system 18a, 18b, 19 configured to generate a varying or moving magnetic field that acts on (i.e transmits power to) a motor portion of the pump module 12 in the disposable delivery unit when the units 2, 4 are positioned close together. The base unit may advantageously comprise a lower application face 13 with a cavity portion forming a docking interface 11 substantially complementary in shape to the upper non mounting face of the delivery unit 2 that forms a complementary docking interface 17, such that the base unit can be guided and positioned over the delivery unit. To this effect, the cavity portion may be provided with a funnel shaped entry portion 15 to help guide and position the base unit over the delivery unit. The dimensions $D_2$ of the cavity portion may be slightly greater than the outer dimensions $D_1$ of the delivery unit to allow a layer of clothing fabric, such as a shirt, to be positioned between the units. This advantageously enables a patient to position the base unit discretely over the delivery unit without removing the last layer of clothing, and furthermore allows for convenient docking of the base unit over the delivery unit as there is some spare space.

Figure 3:
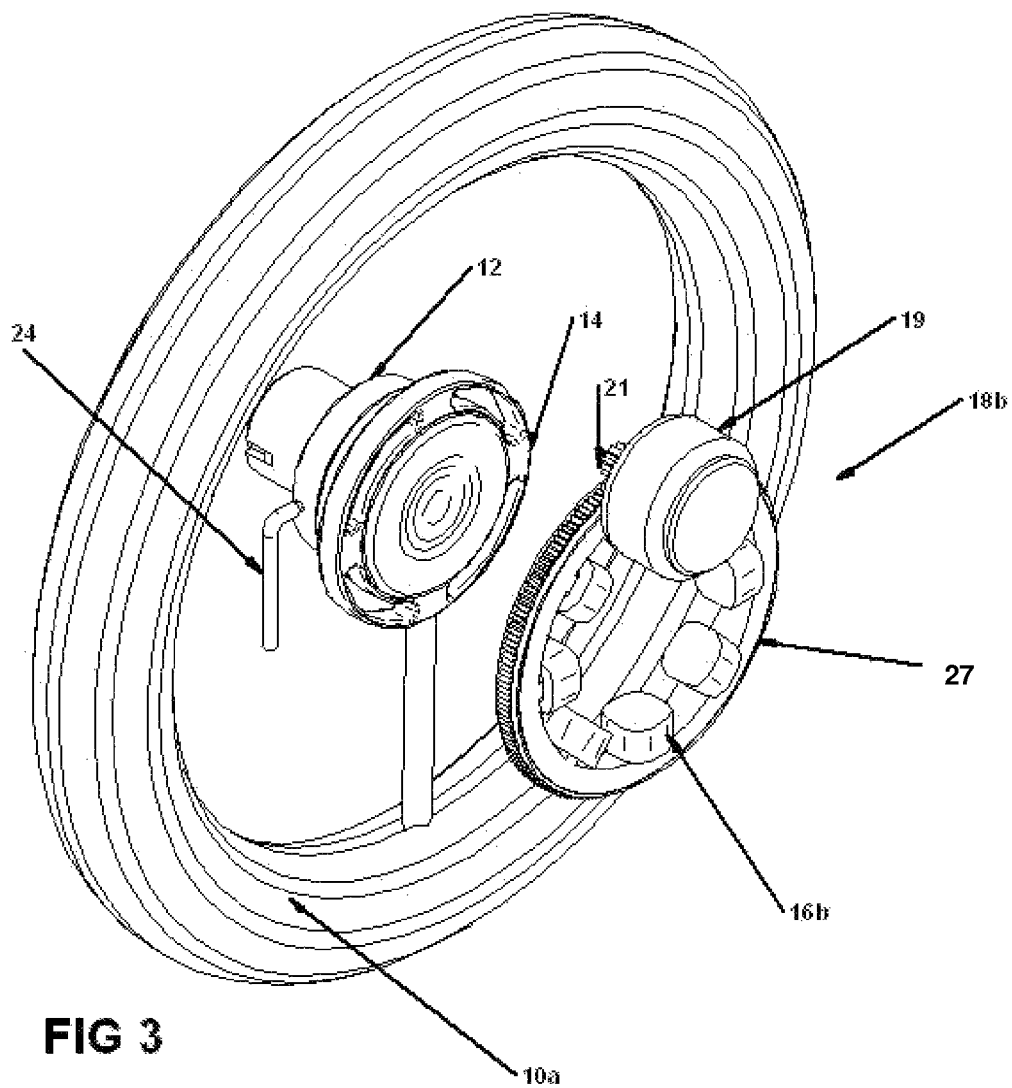
FIG. 3 shows a perspective view of an embodiment of part of the drug delivery device according to the invention, without housing parts.
Figure 4:
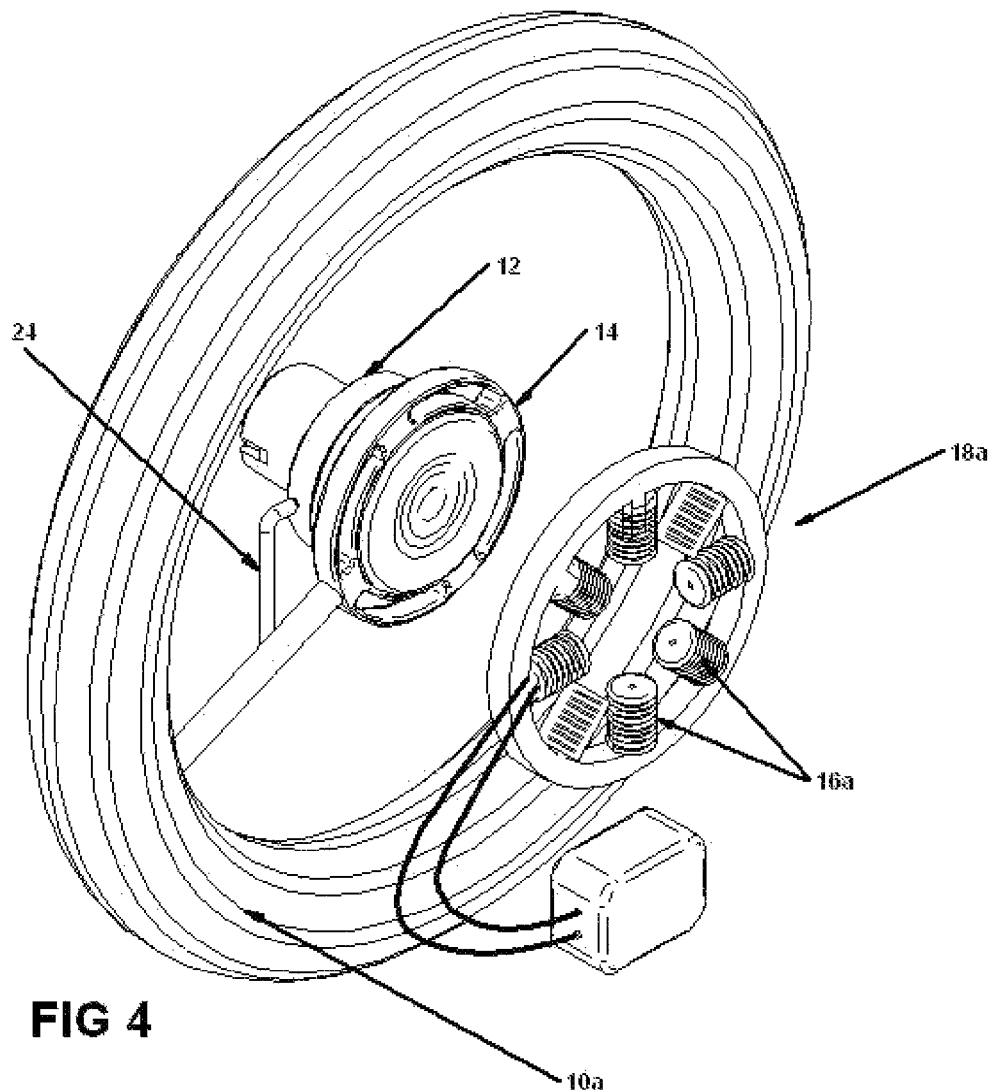
FIG. 4 shows a perspective view of another embodiment of part of the drug delivery device according to the invention, without housing parts.

In the embodiments illustrated, the pump 12 of the disposable delivery unit 2 comprises a rotor 14 having a motor portion in the general form of a cylindrical disc in which are mounted one or more permanent magnets providing a plurality of magnetic poles therearound. In the embodiment illustrated in FIG. 4, the permanent magnets on the pump rotor are driven in rotation by electromagnets 16a arranged in the drive module 18a of the re-usable base unit 4. In the embodiment illustrated in FIG. 3, the permanent magnets on the pump rotor are driven in rotation by magnets 16b arranged on a rotor 27 driven in rotation by a motor 19 via a gear reduction mechanism 21, in the drive module 18b of the re-usable base unit 4.

In use, in order to activate the pump to deliver a dose of medicament, the user approaches the base unit to the delivery unit, e.g. by docking the base unit against the delivery unit, to bring the electromagnets 16a, or magnets 16b, in the drive module into electromagnetic or magnetic power communication (i.e. contactless power communication) with the permanent magnets on the rotor, thus driving the rotor in rotation. The base unit may be placed over and against the delivery unit in direct contact, or indirect contact such as through clothing.

The rotor magnet poles and drive module electromagnets or permanent magnets may advantageously operate as a step motor that allows accurate angular stopping, starting and forward or reverse movement of the rotor to enable accurate dosing of medicament via the pump.

In an alternative embodiment, the varying magnetic field generated by the drive module may act on a coil or a plurality of coils or other transformer device (not shown) mounted in the delivery unit thereby inducing electrical power in the coils via a transformer effect. The induced electrical power may be used to drive a pump motor contained in the delivery unit.

The housing 6 has a lower mounting surface 20 to which is attached an adhesive layer for mounting the delivery device directly on to the skin of a patient.

A needle or canula 22 extends from the outlet 24 of the pump 12, out of the lower mounting surface 20 of the delivery device. The canula can be inserted by means of a removable needle (not shown). The outlet of the pump could alternatively be attached to a catheter suitable for trans-dermal drug delivery, whereby the injection or entry site could be spaced from the disposable delivery unit. In the latter embodiment, the outlet of the pump may extend out of a lateral face of the delivery unit rather than through the lower mounting face.

The adhesive layer on the mounting face of the delivery unit is protected, prior to use, by a protective strip (not shown), which is pealed off just prior to use. The needle or canula is inserted into the patient's skin and the delivery unit is fixed on the patient's skin by means of the adhesive base layer.

Advantageously the delivery unit is provided as a closed unit and may be disposed of in its entirety once the liquid in the reservoir has been consumed or for other reasons, such as after a certain period of use requiring a change in injection point.

The incorporation of the pump, reservoir and injection member in a single closed disposable unit is particularly advantageous since it removes the risks of manipulations in connecting the pump to the reservoir containing the medicament, and/or the injection member to the pump module, and prevents re-filling of the reservoir and re-use of the pump, the delivery unit being disposed of as a single element.

Advantageously the base unit comprises a user interface, suitably in the form of one or more buttons 28a, 28b and one or more displays 30a, 30b, or a touch sensitive display, to allow the user to set the required dose of medicament and optionally to set and regulate control functions. Suitably the base unit comprises a visual display screen, such as an LED or other digital display screen, to allow the user to visualise dose information such as, for instance, the volume of a dose during the setting of the dose amount by the user, the amount of at least the last delivered dose of medicament, and/or the time elapsed since the last administered dose of medicament.

In a preferred embodiment the base unit electronics 26 contains a memory device, suitably comprising or included in an electronic memory chip, adapted to monitor one or more of the time elapsed since at least a last delivered dose, the amounts of at least a last delivered dose, and/or the number and/or amount of doses administered over a certain time period, e.g. a day. Information recorded on the memory device may conveniently be monitored by the user via the user interface and display screen. In this way a user can easily and conveniently monitor the administration of their medicament, i.e. of bolus insulin doses.

The memory device may optionally provide an alarm function by which a user may be alerted if the delivery unit has been activated to deliver doses of mendicant too frequently or too infrequently. The base unit may comprise a visual, a vibrating, or audible alarm, such as a flashing light or buzzer, to alert the user. Alternatively such information may be displayed on the display screen. The user interface may advantageously provide a function for setting and regulating the alarm function by the user.

The base unit may further advantageously comprise a glucose measurement device 32, comprising a glucose measurement sensor as known in the art, connected to the base unit electronics 26 which may use the glucose level information in calculating the dose of medication to administer, and/or in calibrating an implanted continuous second glucose sensor.

The drug delivery device according to the present invention is advantageously used in the trans-dermal administration of a plurality of discrete doses of a medicament to a patient in need thereof, for instance in the administration of bolus insulin in the treatment of diabetes.

The drug delivery device illustrated may be operated according to one embodiment of the invention by fixing the disposable delivery unit to a user's skin, setting the desired dose of medicament on the base unit via the user interface, and bringing the separate reusable base unit temporarily into power and information communication with the delivery unit by bringing the base unit into proximity with the worn delivery unit, for instance by docking the base unit over the delivery unit in direct contact or through clothing, such that the pump is activated to pump a dose of medicament from the reservoir to the injection member.

Between doses the base unit may conveniently be transported by the user, for instance in a pocket or handbag.

The invention claimed is:

1. A drug delivery device for providing a plurality of discrete doses of a medicament comprising:
    a disposable delivery unit configured to be worn by a patient, comprising a reservoir for holding a medicament to be delivered, an injection member adapted for trans-dermal drug delivery, a pump for pumping the medicament to be delivered from the reservoir to the injection member, and an outer docking interface; and
    a separate reusable base unit configured to be carried separately from the disposable delivery unit between administration of said plurality of discrete doses of a medicament while the delivery unit is worn by the patient and to be temporarily placed in contactless power communication with the delivery unit for administration of said discrete doses of a medicament, comprising a drive module providing power for driving the pump to deliver a dose of the medicament, and a complementary outer docking interface configured for placement against the outer docking interface of the delivery unit, such that the base unit is guided when it is temporarily positioned over the delivery unit for bringing the base unit into electromagnetic or magnetic power communication with the delivery unit without mechanical attachment between the delivery unit and base unit.

2. The drug delivery device according to claim 1, wherein the delivery unit comprises an adhesive base adapted for adhesive mounting of the delivery unit on a patient's skin.

3. The drug delivery device according to claim 2, wherein the base unit comprises a memory device adapted to monitor one or more of the amounts of at least a last delivered dose, the time elapsed since one or more doses, and/or the number and/or amount of doses administered over a certain time period.

4. The drug delivery device according to claim 3, wherein the memory device comprises an alarm function.

5. The drug delivery device according to claim 3, wherein the memory device comprises a reminder function.

6. The drug delivery device according claim 1, wherein the base unit comprises a power supply and electronics for controlling operation of the pump and a user interface.

7. The drug delivery device according to claim 1, wherein the injection member is an injection needle or a canula.

8. The drug delivery device according to claim 1, wherein the delivery unit contains a capacitor adapted to activate an alarm if a parameter of the delivery unit is outside a predefined range.

9. The drug delivery device according to claim 1, wherein the pump comprises a drive module comprising a rotor with permanent magnets.

10. The drug delivery device according to claim 9, wherein the drive module comprises electromagnets for driving the permanent magnets disposed on the rotor of the delivery unit pump, or for inducing electrical current in one or more coils in the delivery unit.

11. The drug delivery device according to claim 9, wherein the drive module comprises permanent magnets on a rotor and a motor configured to drive the rotor in rotation, for driving the permanent magnets disposed on the rotor of the delivery unit pump, or for inducing electrical current in one or more coils in the delivery unit.

12. The drug delivery device according to claim 9, wherein the rotor and drive module operate as a stepping motor.

13. The drug delivery device according to claim 1, wherein the delivery unit comprises a transformer coil or coils configured to receive power from a varying magnetic field generated by the base unit.

14. The drug delivery device according to claim 1, wherein the base unit comprises a lower application face with a cavity portion substantially complementary in shape to an upper non-mounting face of the delivery unit, such that the base unit can be positioned and guided over the delivery unit.

15. The drug delivery device according to claim 1, wherein the reservoir is a collapsible reservoir or a coil reservoir.

16. The drug delivery device according to claim 1, wherein the medicament is insulin.

17. A method of operating a drug delivery device adapted for pumping discrete doses of a medicament, comprising:
   removably fixing to a patient's skin a disposable delivery unit comprising a reservoir for holding a medicament to be delivered, an injection member adapted for transdermal drug delivery, and a pump adapted for pumping the medicament to be delivered from the reservoir to the injection member;
   placing a separate reusable base unit, comprising a power source and a drive module for driving the pump, temporarily against the delivery unit into electromagnetic or magnetic power communication such that the pump is activated to pump a dose of medicament, without mechanical attachment between the delivery unit and the base unit; and
   removing the separate reusable base unit from the delivery unit after pumping of the discrete dose of medicament while the delivery unit remains fixed against the patient's skin.

18. A method for the treatment of a condition or disease requiring the administration of discrete doses of a medicament, comprising:
   fixing to the skin of a patient in need thereof a disposable delivery unit comprising a reservoir for holding a medicament to be delivered, an injection member adapted for transdermal drug delivery, and a pump adapted for pumping the medicament to be delivered from the reservoir to the injection member;
   docking the base unit temporarily against the delivery unit without mechanical attachment between the delivery unit and the base unit, said base unit comprising a power source and a drive module for driving the pump to deliver a dose of the medicament to the patient;
   transferring power in an electromagnetic or magnetic manner from the base unit to the delivery unit and actuating the pump to deliver a discrete dose of the medicament; and
   removing the separate reusable base unit from the delivery unit after delivery of the dose of medicament while the delivery unit remains fixed against the patient's skin.

19. The method according to claim 18 further including the steps of monitoring dosage and time of administration of at least a last administration and storing monitored values in a memory of the base unit.

20. The method according to claim 18 wherein the medicament is insulin.

21. A method of bolus administration of a medicament to a patient in need thereof comprising:
   providing a disposable delivery unit adapted to be fixed against a patient's skin, said delivery unit comprising a reservoir for holding a medicament to be delivered, an injection member adapted for trans-dermal drug delivery, and a pump adapted for pumping the medicament to be delivered from the reservoir to the injection member,
   providing a separate reusable base unit, said base unit comprising a drive module for driving the pump,
   removably fixing said diposable delivery unit to a patient's skin;
   docking the base unit temporarily against the delivery unit without mechanical attachment between the delivery unit and the base unit;
   activating the pump to deliver a dose of the medicament to the patient; and
   removing the separate reusable base unit from the delivery unit after delivery of the dose of medicament while the disposable delivery unit remains fixed against the patient's skin.

22. The method according to claim 21 further including the steps of monitoring dosage and time of administration of at least a last administration and storing monitored values in a memory of the base unit.

23. The method according to claim 21 wherein the medicament is insulin.

* * * * *

UNITED STATES PATENT AND TRADEMARK OFFICE
CERTIFICATE OF CORRECTION

| | | |
|---|---|---|
| PATENT NO. | : 8,414,532 B2 | Page 1 of 1 |
| APPLICATION NO. | : 12/672003 | |
| DATED | : April 9, 2013 | |
| INVENTOR(S) | : Brandt et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 350 days.

Signed and Sealed this
Thirty-first Day of December, 2013

Margaret A. Focarino
*Commissioner for Patents of the United States Patent and Trademark Office*